United States Patent [19]
Finn

[11] Patent Number: 6,087,159
[45] Date of Patent: Jul. 11, 2000

[54] ODOR CONTROL SYSTEM

[75] Inventor: Larry J. Finn, Marietta, Ga.

[73] Assignee: Bedminster Bioconversion Corp., Bensalem, Pa.

[21] Appl. No.: 09/051,649

[22] PCT Filed: Jan. 23, 1997

[86] PCT No.: PCT/US97/01023

§ 371 Date: Apr. 6, 1998

§ 102(e) Date: Apr. 6, 1998

[87] PCT Pub. No.: WO97/29832

PCT Pub. Date: Aug. 21, 1997

Related U.S. Application Data

[60] Provisional application No. 60/011,735, Feb. 15, 1996.

[51] Int. Cl.[7] .................................................. B01D 53/85
[52] U.S. Cl. ..................... 435/299.1; 435/290.1; 435/266
[58] Field of Search ................................. 435/266, 290.1, 435/299.1; 422/122; 210/615–618, 150, 151

[56] References Cited

U.S. PATENT DOCUMENTS

| | | | |
|---|---|---|---|
| 4,062,770 | 12/1977 | Kneer | 210/613 |
| 4,723,968 | 2/1988 | Schippert et al. | 95/205 |
| 5,137,687 | 8/1992 | Dunson, Jr. | 422/5.1 |
| 5,160,707 | 11/1992 | Murray et al. | 422/170 |
| 5,175,106 | 12/1992 | Laurenson, Jr. | 435/243 |
| 5,387,036 | 2/1995 | Hagen et al. | 366/346 |
| 5,693,528 | 12/1997 | Grabbe et al. | 435/286.6 |
| 5,858,768 | 1/1999 | Bonnin et al. | |

FOREIGN PATENT DOCUMENTS 4-27415  1/1992  Japan .

*Primary Examiner*—William H. Beisner
*Attorney, Agent, or Firm*—Stanley H. Zeyher

[57] ABSTRACT

An odor control system consisting of a cylindrical bio-scrubber (20) packed with means providing an extensive surface area over which liquid media is caused to cascade, an oxidation pond (22) containing selected microorganism in a fluid media, and means (25) for introducing gases to be treated into the bio-scrubber (20) while concurrently causing microbial-impregnated fluid from the oxidation pond (22) to flow through and into contact with effluent gases passing through the bio-scrubber (20), thereby to effect transport of gases to the oxidation pond (22) where volatile organic compounds are metabolically destroyed. When necessary to achieve optimum odor reduction a further element can be added to the overall combination in the form of a biofilter (30) through which gases emanating from the bio-scrubber (30) are passed before their release to the atmosphere.

4 Claims, 3 Drawing Sheets

ODOR CONTROL SYSTEM

This application claims the benefit of U.S. Provisional Application No. 60/011,735, filed Feb. 15, 1996.

FIELD OF INVENTION

This invention relates to a method and apparatus for removing odors from gaseous emissions and more particularly to an odor control system for use in the treatment of effluents from composting facilities.

BACKGROUND OF THE INVENTION

A primary concern in any process which results in the generation of offensive odors is how to eliminate or reduce such odors and to bring them into acceptable emission levels. The unique system comprising the present invention achieves these ends in an efficient, simple and economic manner. A composing facility, like any other facility who's operation has the potential for offensive odor generation, must operate in a manner that safeguards the public health, safety and the environment. While the invention has wide application to various operating processes, it will be described and illustrated in connection with the co-composting of municipal solid waste and sewage sludge.

Most odors from a composting process result from the incomplete oxidation of organic materials, principally carbohydrates and proteins, in the feed stock. Carbohydrates contain carbon, hydrogen and oxygen in compounds such as cellulose and sugars, which under anaerobic conditions readily decompose and produce odorous compounds such as alcohols, esters, aldehydes and organic acids. Proteins contain carbon, hydrogen, nitrogen, oxygen and sulfur and can produce odorous compounds such as ammonia, amines and mercaptans. By utilizing the present invention, odor emissions from a composting facility can be controlled by the proper design and operation of an aerobic decomposition process and system which converts the odorous compounds into odorless carbon dioxide and water. Such aerobic decomposition occurs primarily in the composting process itself if proper aerobic conditions are maintained. However, it has been found that odor control by the composting process itself cannot typically be expected to reduce odors to acceptable levels. Accordingly, numerous techniques and methods have been employed in an attempt to treat or remove odorous compounds from process effluents. Such methods have included masking or covering an unacceptable odor with an acceptable one; chemical oxidation with agents such as ozone or chlorinated compounds; adsorption onto activated carbon; thermo-oxidation as by incineration; absorption by chemical solutions; or combinations of the above. These methods, on the whole, when applied to composting facilities, have not been too successful.

SUMMARY OF THE INVENTION

A co-composting process typically employs one or more multi-stage digesters in which material being treated undergoes staged microbial decomposition. The conventional digester comprises a tube-like structure divided into two or more compartments or stages. During material processing, the tube is rotated while air is circulated through the digester at controlled rates under predetermined conditions in a flow direction counter to the material flow. This phase of composting is conducted 10 entirely within an enclosed vessel, the only source of odor production is the exhaust air. Typical of such prior art systems and methodology of operation are those set out and described in U.S. Pat. Nos. 3,245,759 and 3,138,447, assigned to the assignee of the subject invention, the teachings of which are hereby incorporated by reference.

A co-composting facility is comprised of three major areas, a tipping floor on which the waste is deposited, a processing area consisting of one or more multi-staged digesters and an aeration or curing area. In a preferred embodiment, the emissions from these various stages of operation are contained within an enclosed structure and conveyed from the enclosure via ducts through the unique odor control system comprising the subject invention. The odor control system comprised a bio-scrubber packed with means over which microbial impregnated water from an oxidation pond is caused to cascade. Effluent air drawn from the composting facility is passed through the bio-scrubber. In passage of the effluents through the scrubber a portion of the volatile organic compounds (VOC'S) are absorbed in the liquid. It is also believed that in some small degree the VOC's are degraded by interaction with the microbial population which deposits itself on surfaces of the bio-scrubber packing. The main mechanism for decomposing the VOC's found in the effluent gases pursuant to this invention is carried out in the oxidation pond and the down stream biofilter. As the gas is passed through the cascading water curtain, VOC's are absorbed and carried to an oxidation pond where they are acted on by the resident microbial population. Gas which has been stripped of a portion of its VOC content is then passed through a biofilter where any residual odor-containing effluents are removed.

BREIF DESCRIPTION OF THE DRAWINGS

For the purpose of illustrating the invention, there is shown a preferred embodiment, it being understood, however, that the invention is not limited to the precise embodiment or application shown and described herein.

DETAILED DESCRIPTION OF THE PRESENTLY PREFERRED EMBODIMENT

Figure 1:
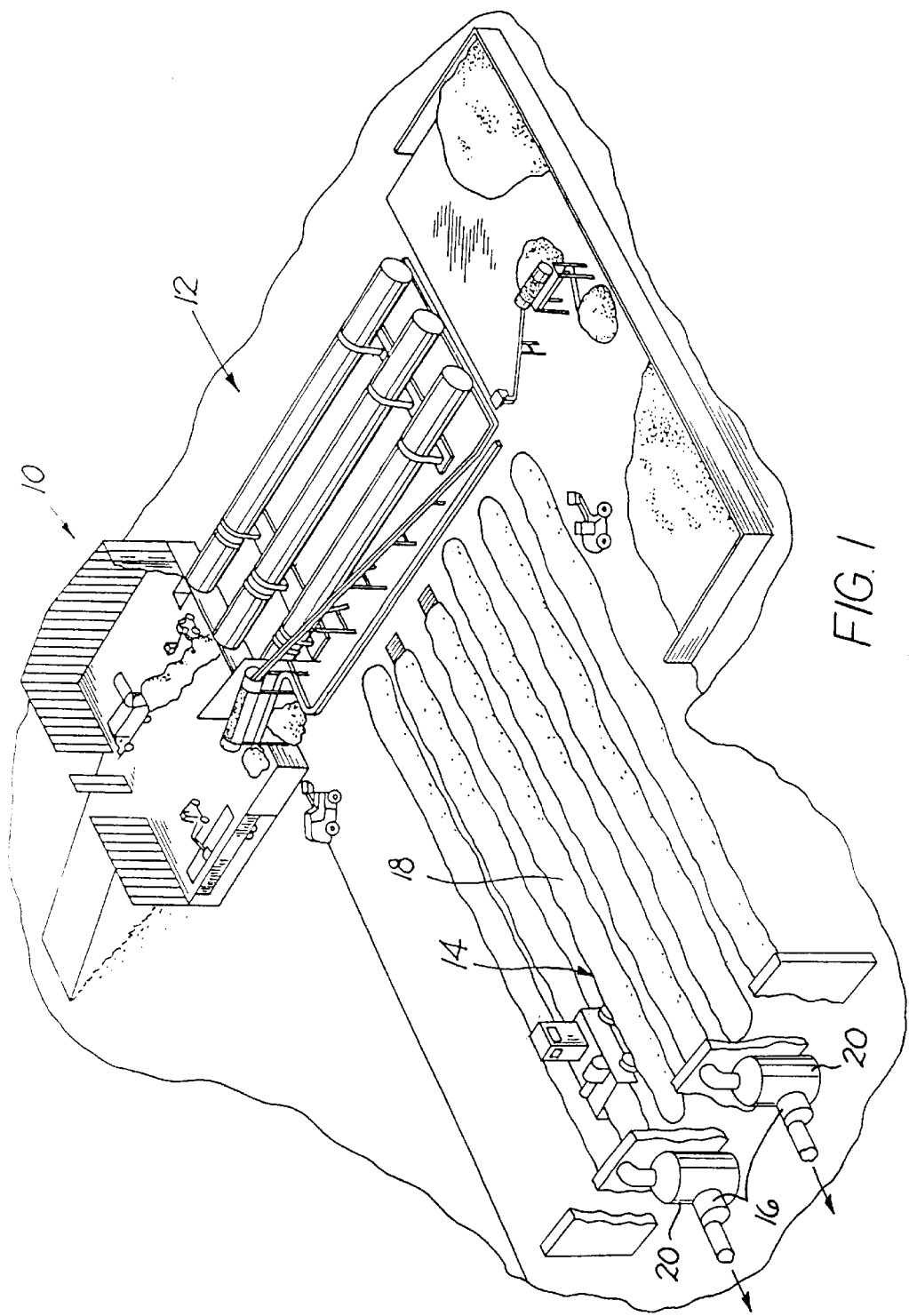
FIG. 1 is a floor plan of an enclosed co-composting facility.
Figure 2:
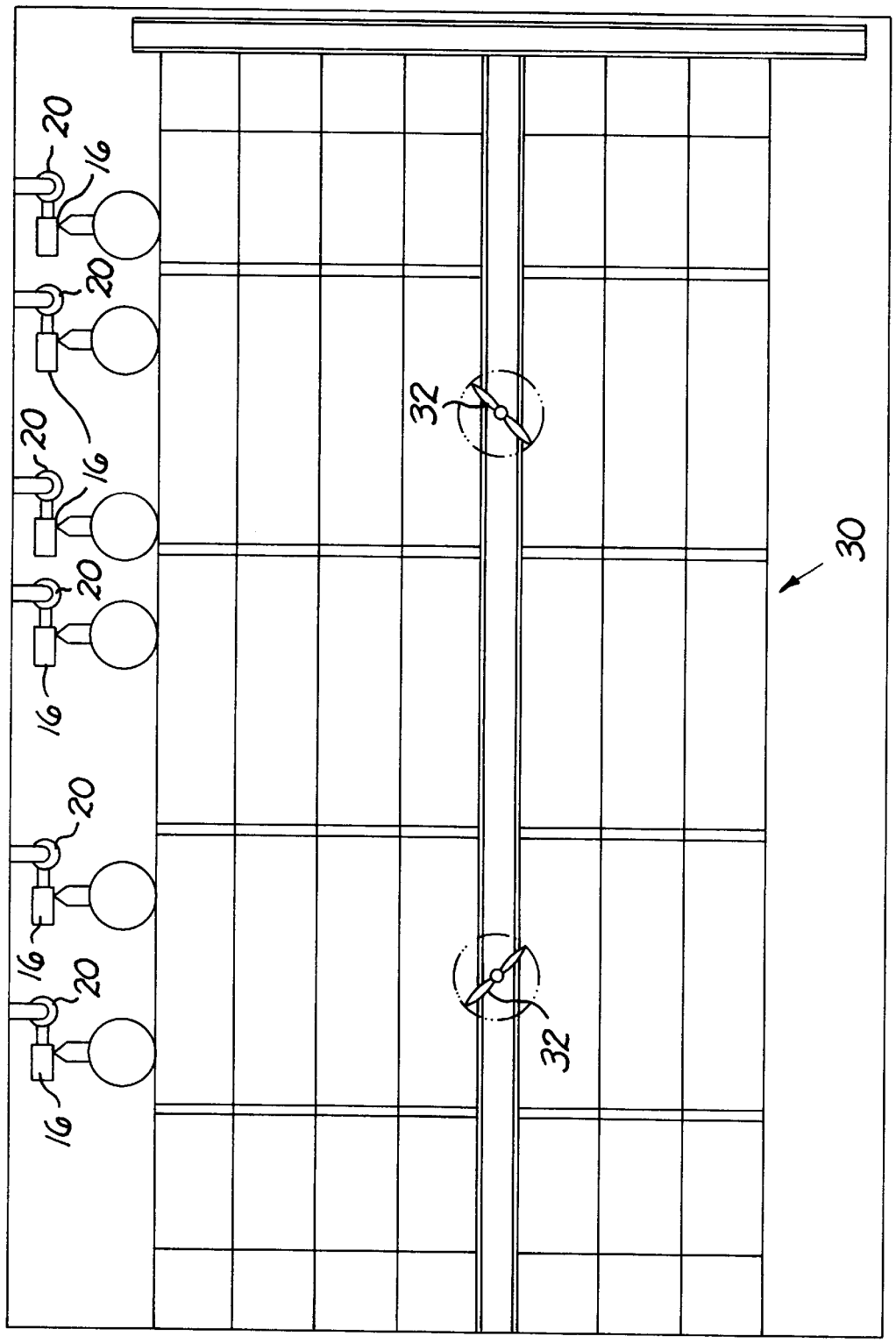
FIG. 2 is a plan view of the odor control system comprising the present invention.
Figure 3:
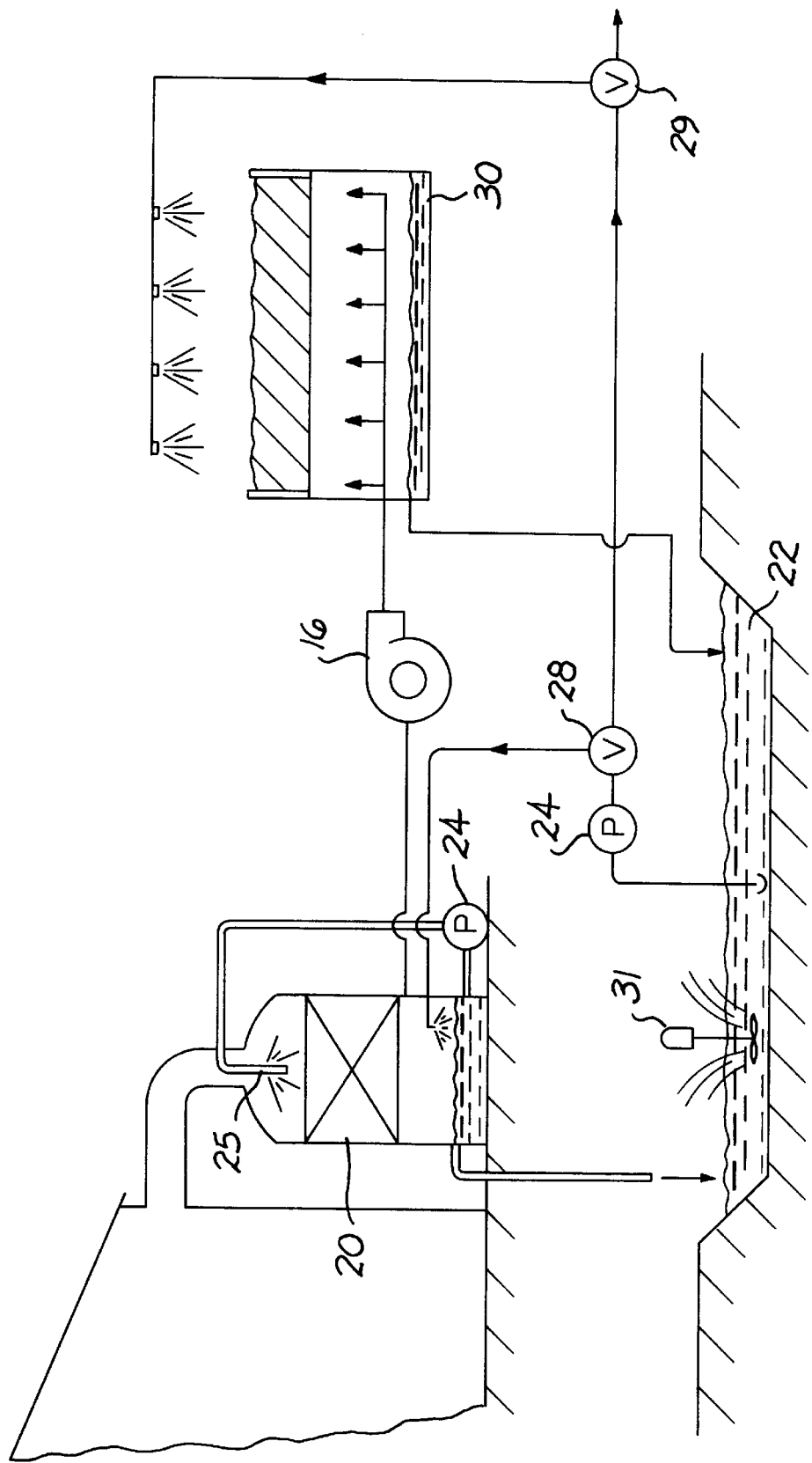
FIG. 3 is an elevational view schematically depicting the overall odor control system.

Referring now to the drawings and more particularly to FIG. 1 thereof, there is shown a floor plan of a completely enclosed composting facility comprised of three major areas; the tipping area 10, a processing area 12 and an aeration or curing area 14. A negative pressure is maintained within the enclosure by means of a battery of blowers 16. The facility is designed to process 300 tons per day of municipal solid waste and utilizes three aeration bays 18 each serviced by two 25,000 cfm blowers. The blowers capture the process gases emanating from each of the major areas of operation and direct the odor laden gases through a series of vertical packed-bed humidification towers or scrubbers 20 as seen in FIGS. 2 & 3. Each of the scrubbers is designed to handle 25,000 cfm of process gases, is 8 feet in diameter, 12 feet 6 inches in overall height and constructed of fiberglass reinforced plastic. After treatment in the scrubber the gases are passed through a biofilter 30 before being released to the atmosphere.

The odor control system comprising the present invention consist in combination, a bio-scrubber 20, an oxidation pond 22 for incubation of selected microorganisms, means 24 and 16 for circulating water and air through the bio-scrubber, and a biofilter 30. As previously noted, the scrubber is cylindrical in configuration and is packed with specially shaped elements providing extensive surface area, low volume and low impedance to fluid flow. This arrangement provides optimum dispersion of water introduced into the scrubber through a PVC water distribution header 25, (FIG. 3) and provides deposition sites for incidental microbial growth. Gases to be treated are introduced into the silo or bio-scrubber either in concurrent or counter flow relation to the water stream at a flow rate of approximately 25,000 cfm. The concurrent flow arrangement is shown in FIG. 3. Water is passed through the bio-scrubber at a flow rate of approximately 400 gpm producing a 1 to 2 second gas residence time in the scrubber. As the water traverses the scrubber, it strips the volatile organic compounds (VOC'S) from the effluent gases. The entrained VOC's are carried into the oxidation pond 22, via the water stream where they are acted on by the pond's microbial population. The oxidation pond is populated with cryophillic microorganisms which metabolically destroy volatile organic compounds. These organisms live in temperature ranges of between 50–104 degrees F. The pond water is recirculated through the bio-scrubber and may also be used, through activation of valve 28, to moisten the biofilter media to achieve a common microbial population. To prevent saturation of the water stream with VOC's and to maintain the water's absorption efficiency, an aerator 31 can be employed, or saturated water can be periodically discharged through valve 29 to a sewer line and replenished with fresh water. VOC's are metabolically deodorized in the pond. As the process of deodorization proceeds sediment comprising live and dead microorganisms settle to the bottom of the pond forming a biomass. In the process of irrigating the biofilter media the biomass is carried by the water stream to the biofilter where the dead organisms are strained out for incorporation into the biofilter media. It is important to the process that the pond water not be overloaded with VOC's. The bio-scrubber is packed with means such as Pall Rings, Tellerette or Jaeger Tri-Pack Type media to provide extensive surface area and to cause a cascading dispersion of the water to form a water curtain to optimize the absorption of VOC's. As a final step in the deodorizing process, gaseous emission from the scrubber are then, depending on the content of volatile organic compounds, either passed into the atmosphere, or directed through a bio-filter 30 for final deodorization before being released to the atmosphere. Test results indicated that up to 50% of the VOC's can be removed before the process gases are sent through the biofilters. The biofilter is as shown and described in U.S. Pat No. 5,583,045 entitled Compost Curing and Odor Control System issued Dec. 10, 1996. The air floor grating underlying the biofilter is as shown and described in U.S. application Ser. No. 08/683,560 filed Apr. 12, 1996 entitled Air Floor Grating. Both inventions have been assigned to the assignee of the present invention and are hereby incorporated by reference. A further feature of the invention is employment of helicopter-type dispersion fans 32, as seen in FIG. 2, which in the event of a thermal inversion are turned on to disperse effluents from the odor control system at substantial atmospheric elevations.

It should also be understood that while the invention has been described in connection with the treatment of gaseous emissions from a composting process, the method of odor control herein described can be used for the removal of odors or VOC's from effluents from different and non analogous sources. It will also be appreciated that having described the present preferred embodiment of the invention with reference to the appended drawings that variations of the formulation of the bacterial population of the oxidation pond can be modified as required by the particular effluents undergoing treatment without departing from the true spirit of the invention as defined in the appended claims.

I claim:

1. Means for deodorizing composting gases, comprising in combination: a container packed with means presenting an extensive surface area to gases traversing the container and said means having low volume and low resistance to the flow of fluid media and gases traversing said container; an oxidation pond containing cryophillic and mesophillic aerobic microorganisms in a fluid media; means for conveying fluid impregnated with said microorganisms to said container for passage over said packing means; means for directing gases to be deodorized into contact with fluid cascading over said packing means whereby volatile organic compounds entrained in the gases are metabolically acted on both by microbial populations resident on the packing means and are carried by the fluid media into the oxidation pond to be further metabolically degraded and deodorized.

2. Means for deodorizing composting gases comprising in combination: a container packed with means presenting an extensive surface area to gases traversing the container and said means having low volume and low resistance to the flow of fluid media and gases traversing said container; an oxidation pond containing aerobic microorganisms in a fluid media; means for conveying impregnated fluid media to said container for passage over said packing means; means for directing gases to be deodorized into contact with fluid cascading over said packing means whereby volatile organic compounds entrained in the gases are metabolically acted on both by microbial populations resident on the packing means and are carried by the fluid media into the oxidation pond to be further metabolically degraded and deodorized; and a biofilter through which gases emanating from the container are passed before release to the atmosphere.

3. The gas deodorizing means set forth in claim 2 including a ventilating fan for dilution and dispersion of effluents from the biofilter at substantial atmospheric elevations.

4. A system for deodorizing composting gases comprising in combination: a container packed with means presenting an extensive surface area to gases traversing said container, and said means having low volume and low resistance to fluid flow; an oxidation pond containing cryophillic and mesophillic aerobic microorganisms in a fluid media; means for conveying the fluid media to said container for passage over said packing means; means for directing gases to be treated into contact with fluid cascading over said packing means whereby volatile organic compounds entrained in the gases are carried into the oxidation pond to be metabolically degraded and deodorized; a bio-filter through which gases emanating from the container are passed; and an updraft fan for dispersion of effluents from the bio-filter at substantial atmospheric elevations.

\* \* \* \* \*